United States Patent
Weinstein et al.

[11] Patent Number: 5,692,493
[45] Date of Patent: Dec. 2, 1997

[54] TONGUE PROTECTOR

[75] Inventors: Lawrence A. Weinstein, Oneida;
Beverly J. Wallace, Canastota;
Fredrick M. Richards, Clinton;
George Puderbaugh, Manlius; David R. Autote, Chittenango, all of N.Y.

[73] Assignee: Diemolding Corporation, Canastota, N.Y.

[21] Appl. No.: 612,752

[22] Filed: Mar. 8, 1996

[51] Int. Cl.$^6$ .................................................. A61M 15/00
[52] U.S. Cl. ............................... 128/200.23; 128/200.14; 604/77
[58] Field of Search .................. 128/200.14, 200.15, 128/200.18, 200.22, 200.23, 204.11, 203.23, 201.26, 207.14, 207.15, 911, 912; 604/77

[56] References Cited

U.S. PATENT DOCUMENTS

| | | |
|---|---|---|
| 79,015 | 6/1868 | Schulz . |
| 327,237 | 9/1885 | Clark . |
| 374,122 | 11/1887 | Genese . |
| 465,161 | 12/1891 | Chase . |
| 487,873 | 12/1892 | Blackman . |
| 990,277 | 4/1911 | Lauderdale ................ 128/200.15 |
| 3,001,524 | 9/1961 | Maison et al. .............. 128/200.23 |
| 3,854,478 | 12/1974 | Cunningham ................. 604/77 |
| 5,318,523 | 6/1994 | Lu ............................ 604/77 |
| 5,341,801 | 8/1994 | Zechner ................... 128/203.15 |
| 5,368,016 | 11/1994 | Henry ...................... 128/200.23 |
| 5,507,278 | 4/1996 | Karell ..................... 128/200.23 |

*Primary Examiner*—Vincent Millin
*Assistant Examiner*—William J. Deane, Jr.
*Attorney, Agent, or Firm*—August E. Roehrig, Jr.

[57] ABSTRACT

A removable single-user tongue shield that is releasably attachable to the dispensing opening of a metered dose inhaler. The tongue protector is shaped to conform to the upper surface of the tongue to cover the taste sensor areas, and to minimize contact of the medication spray with the tongue's surface. In this manner the user is protected from objectionable medication taste while the delivery of the medication into the trachea is unaffected by the protector.

20 Claims, 4 Drawing Sheets

000
TONGUE PROTECTOR

BACKGROUND OF THE INVENTION

This invention relates in general to devices for protecting the tongue of one who uses medication which is administered by a pressurized spray or mist directed into the mouth, over the tongue, and into the throat area.

More specifically, but without restriction to the particular embodiments and/or uses which are shown and described for purposes of illustration, this invention relates to an inexpensive, non-sterile, single user tongue protector which is readily attachable to a medication dispenser such as a metered dose inhaler.

The tongue protector covers the tongue to minimize contact between the tongue and the medication mist without effecting drug delivery to the lungs. In one embodiment the tongue protector may be folded upon itself providing a cover for the opening of the medication dispenser to which the protector may be attached.

As is known to those care givers involved in inhalation therapy, when it is necessary for a patient to self administer medication by inhaling the medication in the form of a mist sprayed into the mouth, many patients find the taste of the medication that settles on the tongue to be quite objectionable. In addition to the medication being objectionable in taste, a long-term application of some of the medications used in such therapy, settling on the tongue, can have negative physiological effects on the tongue itself. Subjecting the tongue to certain medications used in such therapy for a prolonged period of time, can even atrophy the tongue.

The present invention not only covers the tongue to minimize contact with the spray, but aids in correctly positioning the delivery device in the patient's mouth. In one embodiment of the invention, the tongue protector is provided with a guide to inform a user that the spray applicator is correctly positioned to best administer the spray into the trachea.

SUMMARY OF THE INVENTION

It is, therefore, an object of the present invention to improve apparatus for use with the pressurized dispensing of medication by means of a mist or spray administered through the mouth.

Another object of this invention is to cover the taste sensor areas of the tongue, when in use, to minimize contact of these areas with the medication being applied.

A further object of this invention is to assist a user of metered dose inhaled drugs in properly positioning the pressurized medication dispenser for discharging the medication into the trachea.

One other object of this invention is to cover the dispensing opening of the metered dose inhaler when not in use.

These and other objects are attained in accordance with the present invention wherein there is provided a removable single-user tongue shield that is releasably attachable to the dispensing opening of a metered dose inhaler. The tongue protector is shaped to conform to the upper surface of the tongue to cover the taste sensor areas, and to minimize contact of the medication spray with the tongue's surface. In this manner the user is protected from objectionable medication taste while the delivery of the medication into the trachea is unaffected by the protector.

BRIEF DESCRIPTION OF THE DRAWING

Further objects of the present invention, together with additional features contributing thereto and advantages accruing therefrom, will be apparent from the following descriptions of preferred embodiments of the invention which are shown in the accompanying drawings with like reference numerals indicating corresponding parts throughout, and which are to be read in conjunction with the following drawings, wherein.

DESCRIPTION OF THE PREFERRED EMBODIMENT

Figure 1:
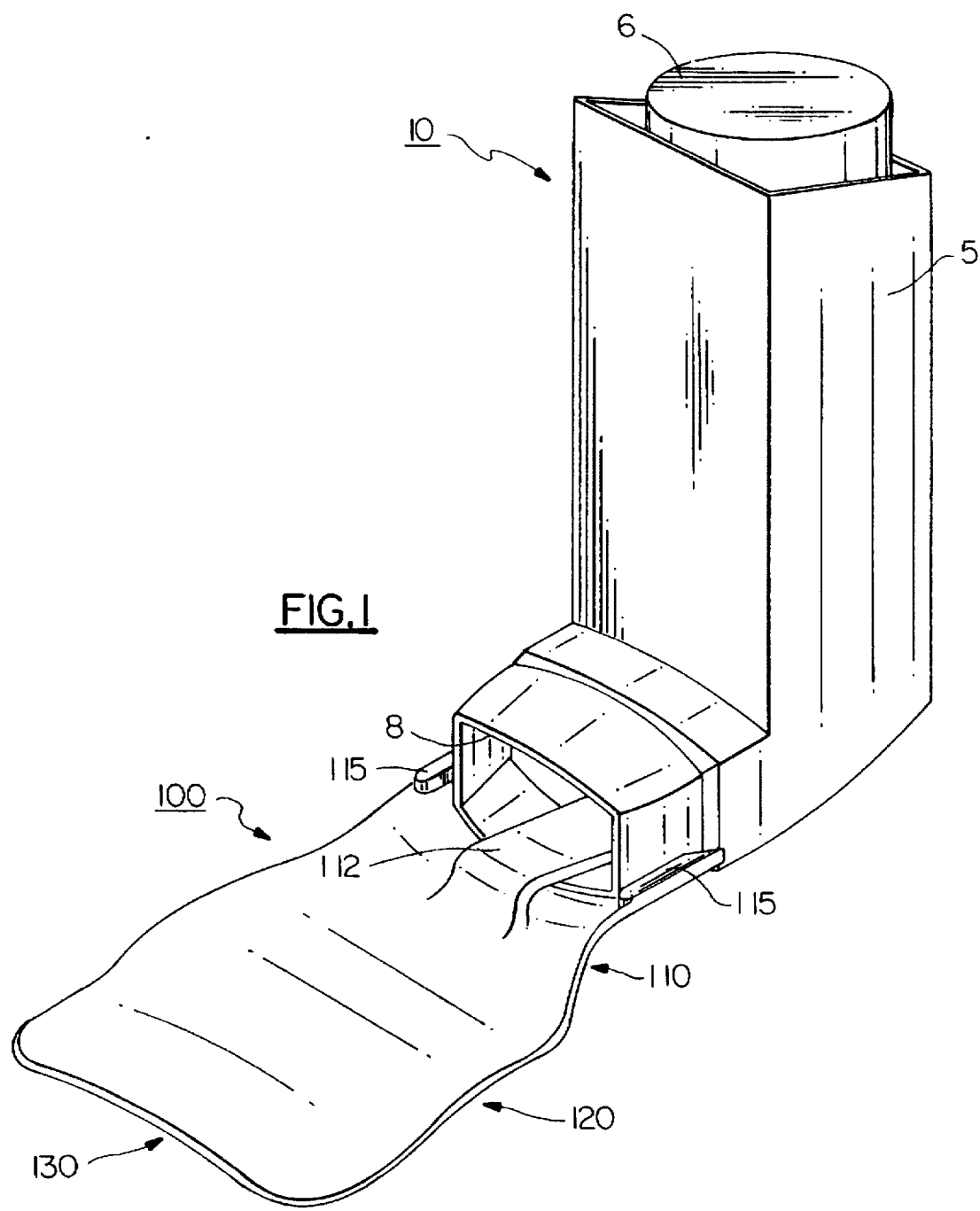
FIG. 1 is a perspective view of one embodiment of the invention attached to a metered dose inhaler.

Referring now to the embodiment of the invention illustrated in FIGS. 1–9, there is shown a tongue protector 100 attached to a metered dose inhaler 10. The metered dose inhaler 10 is of a type commercially available to a respiratory care patient and includes a chamber portion 5 wherein a canister 6 of medication, under pressure, is received to be discharged through a discharge outlet 8. The medication discharge is in the form of a mist or spray which is directed into a patient's mouth, over the tongue, and into the trachea.

The tongue protector 100 comprises a concave shaped dispenser attaching portion 110, by means of which the tongue protector is removably attachable to the medication dispenser 10, a flat planar portion 120 which covers and retains the flat forward portion of the tongue in a proper position for discharge of the medication, and a rear convex shaped cover portion 130 shaped to conform to the upper surface of the rear portion of the tongue. In this manner the tongue protector 100 covers the taste sensor portion of the tongue, while depressing and holding the tongue out from interference with the discharge of medication from the pressurized canister 10, thereby allowing the discharge of medication to be uneffected by the tongue protector 100. Covering the major portion of the tongue surface which would be exposed to the spray or mist, minimizes contact with the spray or mist and thereby minimizes exposure to objectionable tastes and potential harmful physiological effects of prolonged exposure to the medication.

Figure 2:
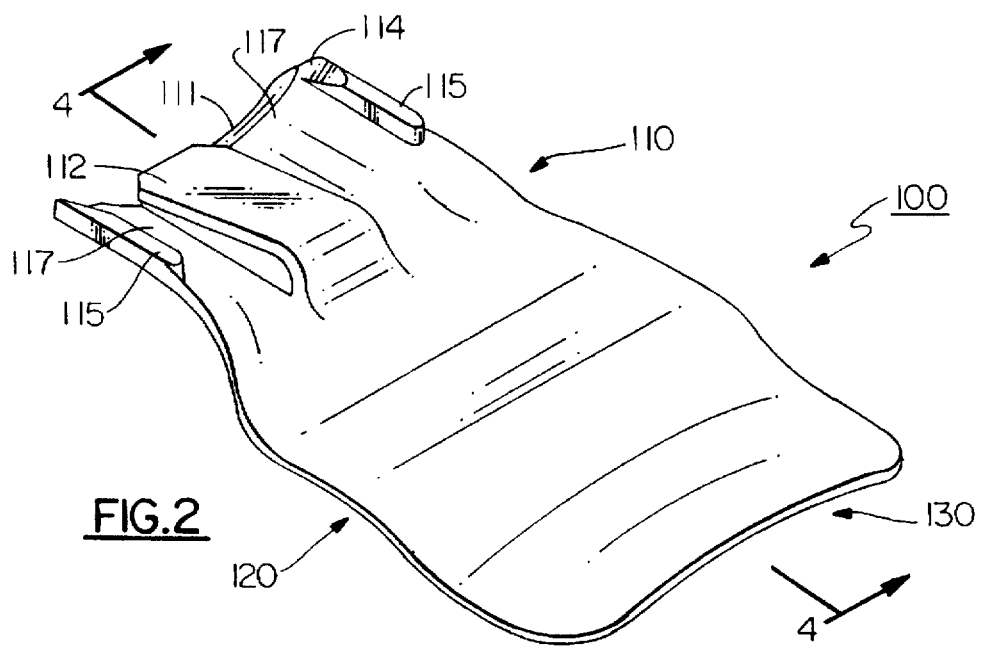
FIG. 2 is a perspective view of the tongue protector illustrated in FIG. 1 showing the upper surface thereof.
Figure 3:
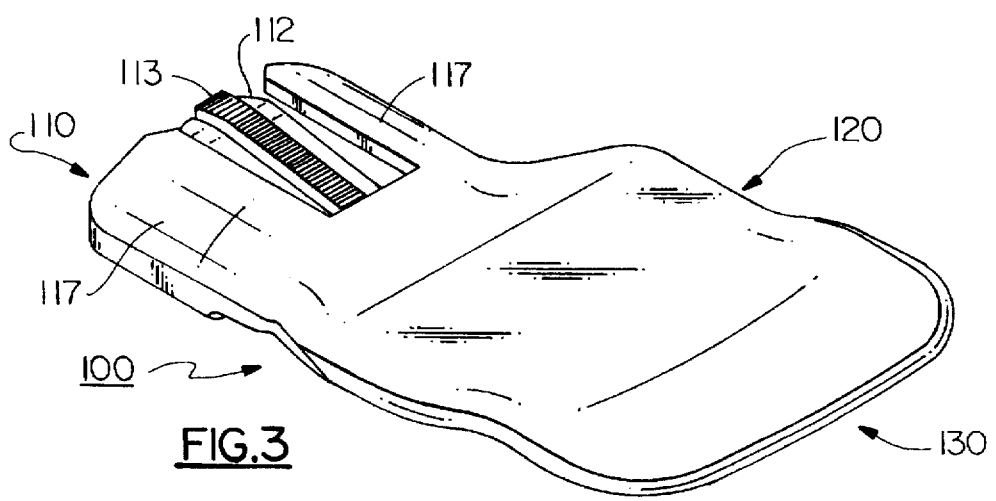
FIG. 3 is a perspective view of the tongue protector illustrated in FIG. 2 showing the reverse side thereof.
Figure 4:
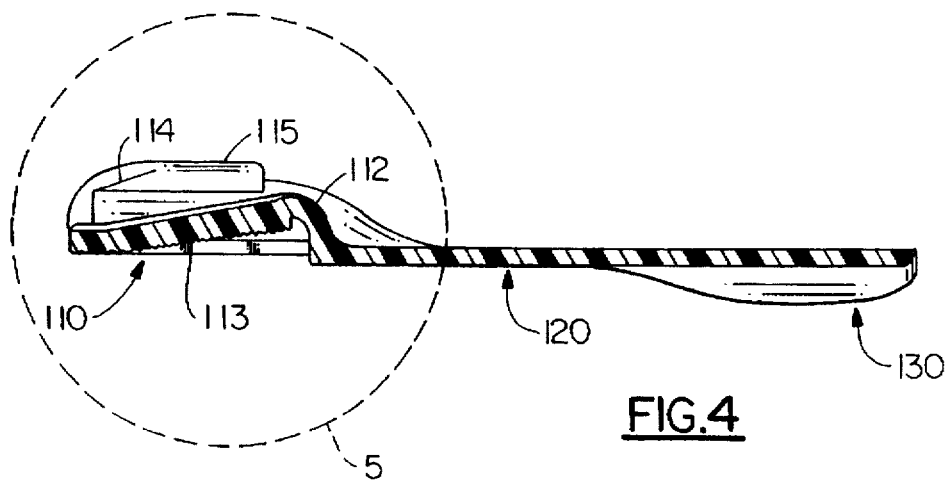
FIG. 4 is a cross-sectional view of the tongue protector illustrated in FIG. 2 taken along line 4—4.
Figure 5:
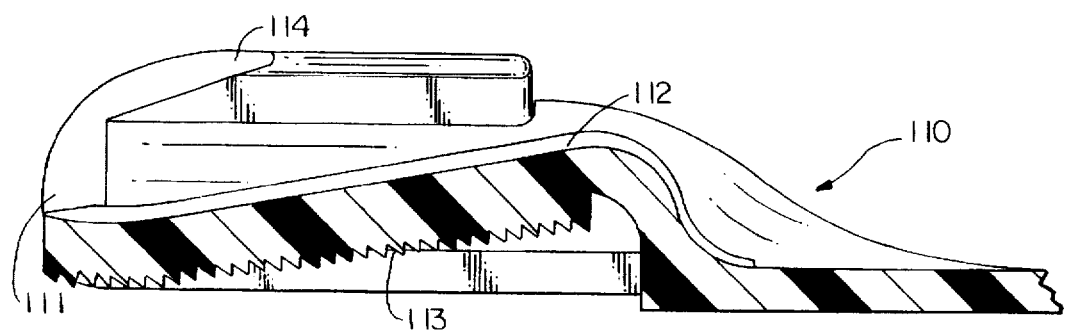
FIG. 5 is an enlarged portion of FIG. 4 as indicated by the encircled portion thereof to better illustrate the attaching portion of the tongue protector.
Figure 7:
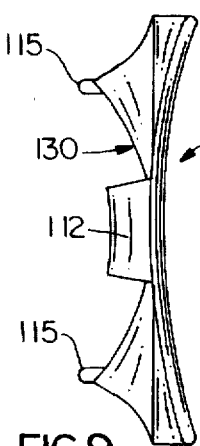
FIG. 7 is an end planar view of the tongue protector illustrated in FIG. 6 in the direction of line 7—7.
Figure 6:
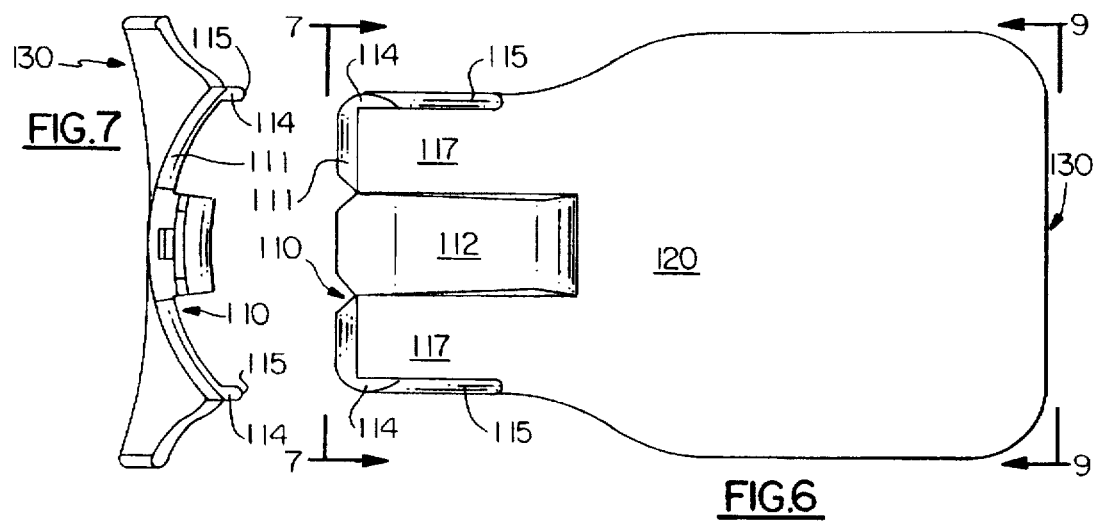
FIG. 6 is a top planar view of the tongue protector illustrated in FIG. 2.
Figure 9:
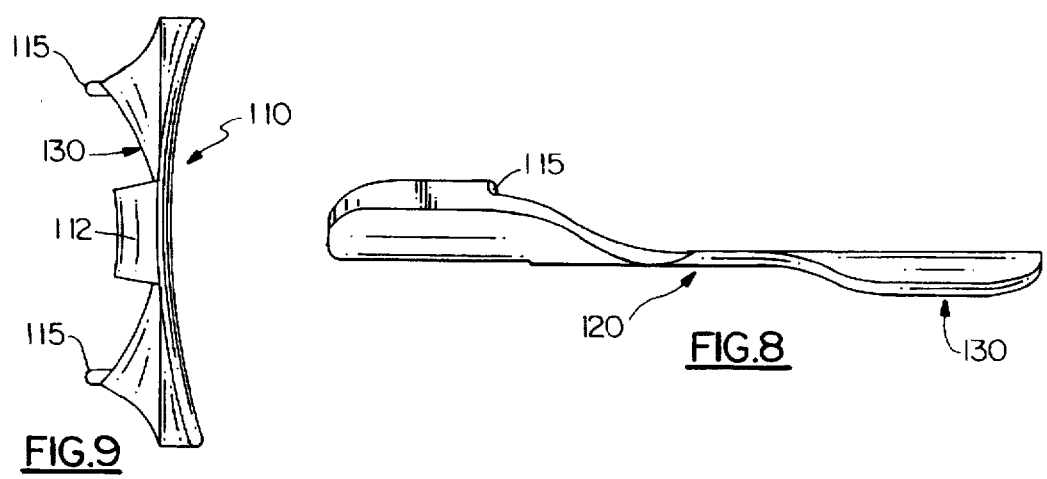
FIG. 9 is an end planar view of the tongue protector illustrated in FIG. 6 in the direction of line 9—9.
Figure 8:
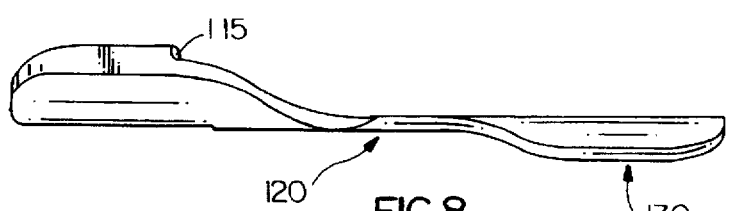
FIG. 8 is a side profile view of the tongue protector illustrated in FIG. 6.

As best shown in FIGS. 2, 3 and 5, the dispenser attachment portion 110 is formed of a width less than the remainder of the tongue protector 100. In practice, a width of about one (1) inch for this portion is preferable, while the width of the remainder of the tongue protector 100 is preferably about one and a half (1½) inches. A cantilevered attaching finger 112 is formed from the front of the dispenser attachment portion 110, and is resiliently biased downwardly to engage the upper inner surface of the lower portion of the discharge outlet or opening 8 of the canister chamber or holder 5 for holding the tongue protector 100 in position on the canister holder as illustrated in FIG. 1. The front of the dispenser attachment portion 110, from which a portion was used to create the cantilevered attaching finger 112, thereby becomes bifurcated. The two bifurcated portions 117 thereby created, with the attaching finger 112 carried therebetween, are used to removably secure the tongue protector 100 to the discharge outlet 8 of the pressurized medication dispenser 10, with the resilient downwardly-biased attaching finger 112 pressing downwardly on the inner or upper surface of the lower portion of the discharge outlet 8, and the bifurcated portions 117 being held against the outer or lower surface of the lower portion of the discharge outlet 8.

The lower surface of the attaching finger 112 has formed thereon a series of serrations 113, best shown in FIG. 5, to assist in securing the attachment to the dispenser. The leading edge 111 of the dispenser attachment portion 110, and the leading edge 114 of each guide 115 positioned at the front edges of the dispenser attachment portion 110, are tapered to assist in the attachment of the tongue protector to the discharge opening 8. The guides 115 provide an abutment against which one or both of the canister discharge opening side walls can contact to facilitate attachment of the tongue protector.

Figure 10:
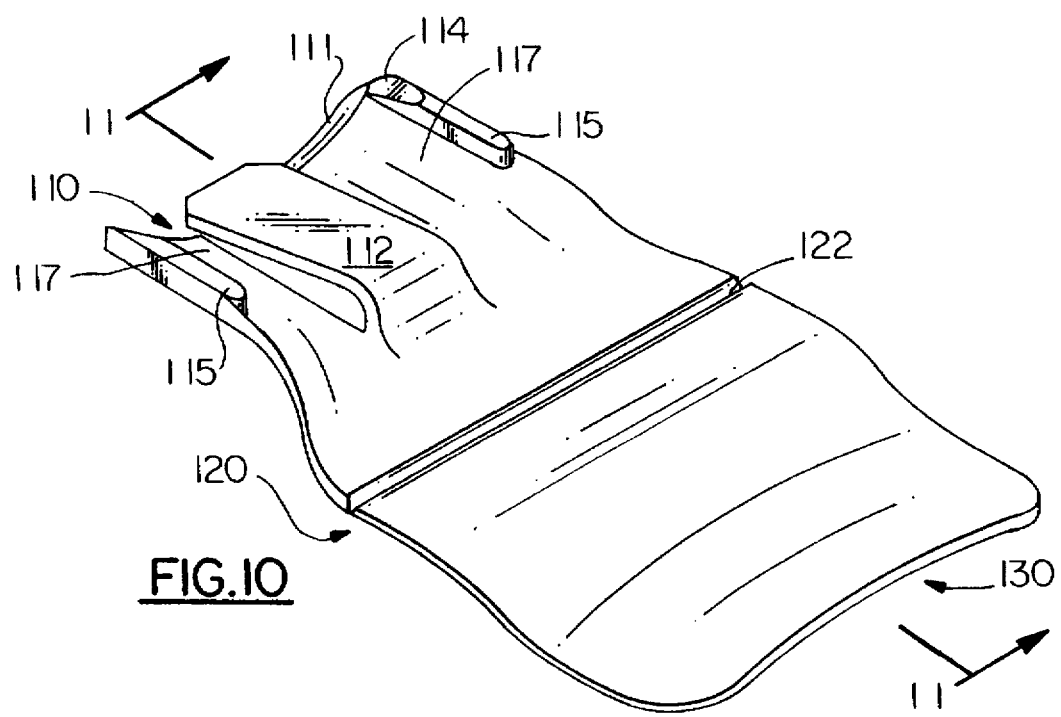
FIG. 10 is a perspective view of an alternative embodiment of the tongue protector illustrated in FIGS. 1–9, to illustrate a hinge portion enabling the tongue protector to be folded to cover the discharge opening of a metered dose inhaler to which it may be attached.
Figure 11:
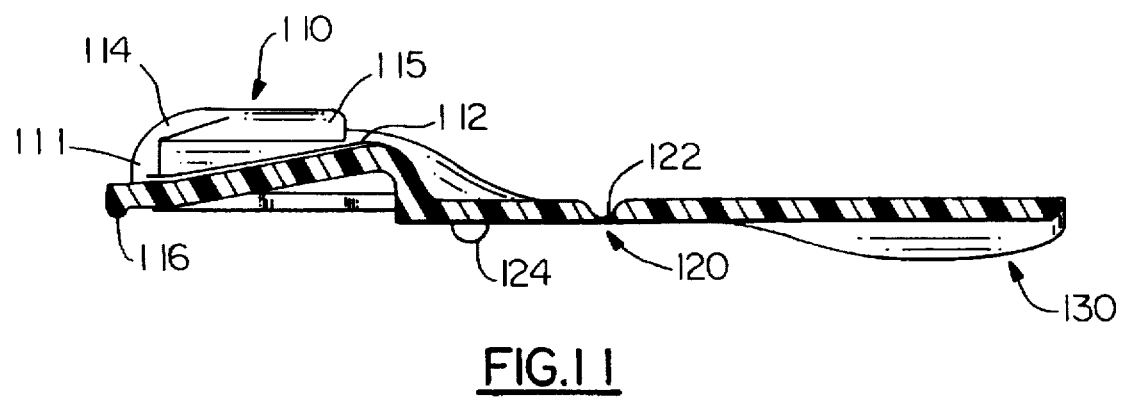
FIG. 11 is a cross-sectional view of the embodiment of the tongue protector illustrated in FIG. 10 taken along line 10—10.

Referring now to the alternative embodiment illustrated in FIGS. 10 and 11, a living hinge 122 is formed in the planar portion 120 by removal of a portion of the material, preferably plastic, from which the tongue protector is formed. The hinge 122 so formed enables the rear portion 130 of the protector to be folded to provide a cover for the discharge opening of the canister holder when the tongue protector is attached thereto. In addition, a retaining stop 116 is formed at the leading edge of the attaching finger 112 to assist in securing the tongue protector to a canister holder, especially those canister holders of the type having an internal ridge inside the discharge opening which the retaining stop can engage. A further alternative is the provision of a positioning stop 124 on the lower surface of the planar portion 120 to assist a user in the proper placement of the tongue protector in the mouth. When the tongue protector is in use, contact of the user's lower front teeth or the tip of the user's tongue with the positioning stop 124 will inform the user that the tongue protector is in the proper position for administering the medication.

While this invention has been described and explained with reference to preferred embodiments, the structures of which have been disclosed herein, it will be understood by those skilled in the art to which this invention pertains that various changes may be made and equivalents may be substituted for elements thereof without departing from the invention. For example, the serrations formed on the bottom surface of the attaching finger may be removed in certain applications. In addition many other modifications, such as the addition of other features or the repositioning of the stops or hinge could be effected. Therefore, it is intended that the invention not be limited to the particular embodiments disclosed in the specification and shown in the drawings as the best mode presently known by the inventors for carrying out their invention, nor confined to the details set forth in this specification, but that the invention will include all embodiments, modifications and changes as may come within the scope of the following claims:

What is claimed is:

1. A tongue cover for use with a dispenser of pressurized medication administered into the throat through a user's mouth, the tongue cover comprising a first concave-shaped dispenser attachment portion for connecting the tongue cover to a dispenser of pressurized medication having a discharge outlet through which the pressurized medication contained therein is discharged, said dispenser attachment portion including an attaching finger removably insertable into the discharge outlet of the pressurized medication dispenser for releasably connecting the tongue cover to the discharge outlet, said attaching finger having one end connected to said dispenser attachment portion and a free distal end resiliently biased downwardly for engagement with a portion of the pressurized medication dispenser discharge outlet, said dispenser attachment portion further including a bifurcated forward portion with said attaching finger positioned between said bifurcated forward portion to receive the dispenser discharge outlet opening between said attaching finger and said adjacent bifurcated forward portion, and a second cover portion conforming substantially to the shape of the upper surface of a user's tongue for covering the sensor areas thereof to minimize contacting the tongue with the medication dispensed through the discharge outlet of the pressurized medication dispenser.

2. The tongue cover of claim 1 wherein said attaching finger includes means for securing said attaching finger to the dispenser discharge outlet when inserted therein.

3. The tongue cover of claim 2 wherein said means for securing said attaching finger to the dispenser discharge outlet when inserted therein includes serrations on the surface of said attaching finger which engage the dispenser discharge outlet.

4. The tongue cover of claim 3 wherein said serrations are formed on a lower surface of said attaching finger.

5. The tongue cover of claim 2 wherein said means for securing said attaching finger to the dispenser discharge outlet when inserted therein includes a retaining stop for engaging a portion of the dispenser discharge outlet.

6. The tongue cover of claim 1 wherein said dispenser attachment portion further includes an attaching guide positioned adjacent an outer edge of each bifurcated portion for engaging the dispenser discharge outlet to facilitate connection therewith.

7. The tongue cover of claim 6 wherein a leading edge of each attaching guide and a leading edge of the dispenser attachment portion are tapered to facilitate engagement with the dispenser discharge outlet.

8. The tongue cover of claim 1 further including a positioning stop carried by said second cover portion to facilitate proper positioning of the dispenser for discharge of the pressurized medication contained therein.

9. The tongue cover of claim 1 further including a hinge carried by said second cover portion for folding at least a part of said second cover portion to a position covering the dispenser discharge outlet.

10. The tongue cover of claim 9 wherein said hinge is formed in said second cover portion.

11. A dispenser of pressurized medication administered into the throat through a user's mouth, including a tongue cover for minimizing contact of the medication with the user's tongue, comprising a dispensing holder adapted to receive a container of medication which is to be administered under pressure, said dispensing holder actuable to release the medication through a discharge outlet into the throat of a user, a tongue cover connected to said discharge outlet of said dispensing holder, said tongue cover including a first concave-shaped dispenser attachment portion for connecting the tongue cover to said discharge outlet through which the pressurized medication contained therein is discharged, said dispenser attachment portion including an attaching finger removably insertable into said dispensing holder discharge outlet for releasably connecting said tongue cover to said discharge outlet, said attaching finger having one end connected to said dispenser attachment portion and a free distal end resiliently biased downwardly for engagement with a portion of said discharge outlet, said dispenser attachment portion further including a bifurcated forward portion with said attaching finger positioned between said bifurcated forward portion to receive said dispenser discharge outlet between said attaching finger and said adjacent bifurcated forward portion, and a second cover portion conforming substantially to the shape of the upper surface of a user's tongue for covering the sensor areas thereof to minimize contacting the tongue with the medication dispensed through said discharge outlet.

12. The dispenser of claim 11 wherein said attaching finger includes means for securing said attaching finger to said dispenser discharge outlet when inserted therein.

13. The dispenser of claim 12 wherein said means for securing said attaching finger to said dispenser discharge outlet when inserted therein includes serrations on the surface of said attaching finger which engage the dispenser discharge outlet.

14. The dispenser of claim 13 wherein said serrations are formed on the lower surface of said attaching finger.

15. The dispenser of claim 12 wherein said means for securing said attaching finger to said dispenser discharge outlet when inserted therein includes a retaining stop for engaging a portion of said dispenser discharge outlet.

16. The dispenser of claim 11 wherein said dispenser attachment portion further includes an attaching guide positioned adjacent an outer edge of each bifurcated portion for engaging said dispenser discharge outlet to facilitate connection therewith.

17. The dispenser of claim 16 wherein a leading edge of each attaching guide and a leading edge of said dispenser attachment portion are tapered to facilitate engagement with said dispenser discharge outlet.

18. The dispenser of claim 11 further including a positioning stop carried by said second cover portion to facilitate proper positioning of said dispensing holder for discharge of the pressurized medication contained therein.

19. The dispenser of claim 11 further including a hinge carried by said second cover portion for folding at least a part of said second cover portion to a position covering said dispenser discharge outlet.

20. The dispenser of claim 19 wherein said hinge is formed in said second cover portion.

\* \* \* \* \*